United States Patent [19]

Hirsh et al.

[11] Patent Number: 5,643,192

[45] Date of Patent: Jul. 1, 1997

[54] AUTOLOGOUS FIBRIN GLUE AND METHODS FOR ITS PREPARATION AND USE

[75] Inventors: Jack Hirsh, Hamilton; Marilyn Johnston, Millagrove; Kevin Teoh, Ancaster, all of Canada

[73] Assignee: Hamilton Civic Hospitals Research Development, Inc.

[21] Appl. No.: 417,880

[22] Filed: Apr. 6, 1995

[51] Int. Cl.$^6$ .................................................. A61M 37/00
[52] U.S. Cl. .............................. 604/4; 424/530; 424/531; 435/214; 530/382
[58] Field of Search ................... 604/4–6; 424/529–531, 424/94–64; 514/2, 802; 435/214; 530/380, 382

[56] References Cited

U.S. PATENT DOCUMENTS

| | | |
|---|---|---|
| 4,265,233 | 5/1981 | Sugitachi et al. |
| 4,298,598 | 11/1981 | Schwarz et al. |
| 4,362,567 | 12/1982 | Schwarz et al. |
| 4,377,572 | 3/1983 | Schwarz et al. |
| 4,414,976 | 11/1983 | Schwarz et al. |
| 4,427,650 | 1/1984 | Stroetmann . |
| 4,427,651 | 1/1984 | Stroetmann . |
| 4,442,655 | 4/1984 | Stroetmann . |
| 4,453,939 | 6/1984 | Zimmerman et al. |
| 4,627,879 | 12/1986 | Rose et al. |
| 4,655,211 | 4/1987 | Sakamoto et al. |
| 4,909,251 | 3/1990 | Seelich . |
| 5,405,607 | 4/1995 | Epstein ..................... 514/802 |
| 5,411,885 | 5/1995 | Marx ....................... 424/94.64 |

FOREIGN PATENT DOCUMENTS

WO96/17871 6/1996 WIPO .

OTHER PUBLICATIONS

M. Brennan "Fibrin Glue," *Blood Reviews* (1991) 5, 240–244.

L. DePalma et al. "The preparation of fibrinogen concentrate for use as fibrin glue by four different methods," Transfusion (1993) vol. 33, No. 9, 717–720.

P. McCarthy "Fibrin Glue in Cardiothoracic Surgery," *Transfusion Medicine Reviews*, vol. VII, No. 3 (1993) 173–179.

S.A. Cederholm-Williams "Autologous fibrin sealants are not yet available," the Lancet (1994) vol. 344, 336–337.

D. A. Wiegand, et al. "Assessment of Cryoprecipitate-Thrombin Solution for Dural Repair," Head & Neck, (1994) 569–573.

Primary Examiner—John G. Weiss
Assistant Examiner—P. Zuttarelli
Attorney, Agent, or Firm—Townsend and Townsend and Crew LLP

[57] ABSTRACT

A fibrin glue includes a fibrinogen component and a thrombin component, both prepared from single donor plasma. The plasma is precipitated to produce a precipitate containing fibrinogen and a supernatant containing the thrombin. The precipitate may be resuspended in a small volume of supernatant and used as the fibrinogen component. The supernatant is further treated by clotting to convert residual fibrinogen to fibrin and filtration to remove the fibrin. The resulting serum can be used as the thrombin component.

15 Claims, 1 Drawing Sheet

AUTOLOGOUS FIBRIN GLUE AND METHODS FOR ITS PREPARATION AND USE

BACKGROUND OF THE INVENTION

1. Field of the Invention

The present invention relates generally to the preparation and use of tissue adhesives which rely on combining fibrinogen and thrombin. More particularly, the present invention relates to a method for preparing a fibrin glue from plasma components obtained from a single donor, preferably for use in autologous fibrin glues.

Tissue adhesives in the form of fibrin glues have been proposed for use to control bleeding and promote wound healing in a variety of traumatic and surgical situations. Many wounds and surgically created defects are not amenable to conventional suture repair, and the ability to enhance defect closure and inhibit bleeding by promoting clot formation would be advantageous. Fibrin glues contain fibrinogen and thrombin which, when mixed together, form fibrin, the basic substance of clot. In Europe and elsewhere, commercial fibrin glues are prepared from fibrinogen obtained by pooling plasma cryoprecipitate from multiple human donors. The risk of disease associated from such pooled plasma sources, however, has caused such products to be withdrawn from use in the United States.

In order to avoid the risk associated with pooled plasma sources, "autologous" fibrin glues have been proposed where fibrinogen is obtained from plasma from a single donor, often a patient to be treated in a subsequent surgical procedure. Such autologous fibrin glues, however, rely on combining the autologous fibrinogen with bovine thrombin, and thus suffer from the deficiencies associated with use of non-human animal products e.g., an immune response against the bovine plasma proteins.

Prior to the work reported in the present application, it was not apparent that thrombin, as well as fibrinogen, could be obtained from single donor plasma. In particular, it was not apparent that sufficient thrombin could be obtained from the amount of plasma used as a source for the single donor fibrinogen. Furthermore, it would have been expected that thrombin obtained from clotted plasma would be inactivated by plasma antithrombins and would therefore not be suitable for subsequent use in a fibrin glue.

For these reasons, it would be desirable to provide improved fibrin glues and methods for their preparation and use, where the fibrin glues are prepared from fibrinogen and thrombin components obtained from single donor plasma, preferably for use in autologous compositions where the glue is later administered to the donor. It would further be desirable that the thrombin component of such fibrin glues contain sufficient thrombin to produce a solid fibrin gel when mixed with the fibrinogen component, and that the thrombin component remain stable and capable of producing the fibrin gel for at least an hour after preparation.

2. Description of the Background Art

Wiegand et al. (1994) *Head & Neck* November/December, pages 569–573, describes the preparation and use of a fibrin glue having a fibrinogen component obtained by cryoprecipitation of single donor plasma and a bovine thrombin component. The shortcomings of such fibrin glues are discussed in Cederholm—Williams (1994) *The Lancet* 344: 336–337. Review articles discussing various forms of fibrin glue include McCarthy (1993) *Transfusion Med. Rev.* VII: 173–179; DePalma et al. (1993) *Transfusion* 33: 717–720; and Brennan (1991) *Blood Reviews* 5: 240–244. U.S. Pat. No. 4,627,879, describes the preparation of fibrinogen by cryoprecipitation of plasma from a single donor. While combination with "human" thrombin is suggested, no source of technique for obtaining human thrombin is provided, and the only specific source of thrombin mentioned is commercial bovine thrombin. Other U.S. Patents relating to tissue adhesives include U.S. Pat. Nos. 4,909,251; 4,655,211; 4,453,939; 4,442,655; 4,427,651; 4,427,650; 4,414,976; 4,377,572 4,362,567; 4,298,598; and 4,265,233.

SUMMARY OF THE INVENTION

According to the method of the present invention, fibrin glues may be prepared from plasma obtained from a single donor as follows. Fibrinogen is first precipitated from the plasma to produce a precipitate and a supernatant. The supernatant is separated from the precipitate, and residual fibrinogen in the supernatant is removed by clotting to produce serum. The fibrin glue thus comprises a first component including the precipitate which contains the fibrinogen and a second component including the clotted serum which contains the thrombin. Precipitation of fibrinogen from the plasma may be performed in any conventional manner, including cryoprecipitation, polyethylene glycol precipitation, ammonium sulfate precipitation, and the like. Usually the fibrinogen concentration in the precipitate will be at least about 20 g/l. Optionally, the fibrinogen precipitate may be resuspended with a portion of the supernatant prior to recombination with the thrombin-containing serum. The residual fibrinogen may be clotted from the supernatant in any conventional manner, such as by the addition of calcium chloride, or the like. Surprisingly, it has been found that the thrombin component of the fibrin glues prepared by this method have substantial thrombin activity, typically having a thrombin activity greater than 5 U/ml immediately following clotting usually having a thrombin activity greater than 20 U/ml immediately following clotting. The thrombin component also retains substantial activity over extended periods, usually having a thrombin activity greater than 2 U/ml one hour after clotting, preferably having a thrombin activity greater than 5 U/ml one hour after clotting, and often having an activity greater than 10 U/ml one hour after clotting.

The present invention further provides a method for preparing a thrombin composition, where fibrinogen is precipitated from single donor plasma to produce a fibrinogen-containing precipitate and a thrombin-containing supernatant. Residual fibrinogen in the supernatant is then clotted to produce serum containing thrombin and fibrin. The thrombin composition is then completed by separating fibrin from the clotted serum, usually by filtration. The fibrinogen may be clotted by any of the techniques described above, and the thrombin compositions will have the thrombin activities set forth above.

The present invention further provides improved fibrin glues of the type including a fibrinogen component obtained from a single donor and a thrombin component. As discussed in the Background section above, such fibrin glues have typically employed thrombin obtained from non-human sources, such as bovine thrombin. The improvement of the present invention comprises obtaining the thrombin component from the same, single donor. In particular, the thrombin component is obtained by precipitating fibrinogen from donor plasma to produce a supernatant and clotting residual fibrinogen in the supernatant to produce the thrombin component. The thrombin component will preferably have the activities set forth above.

The present invention still further provides a method for administering a fibrin glue to a patient, where the method comprises applying to a treatment site on the patient a fibrin glue including a fibrinogen component and a thrombin component prepared as described above.

The present invention still further comprises an improved method for administering a fibrin glue to a patient, wherein the method is of the type where a fibrinogen from a single donor and thrombin are combined and applied to a treatment site on the patient. The improvement comprises obtaining the thrombin from the same donor that supplied the fibrinogen. Typically, the donor and the patient will be the same person.

DESCRIPTION OF THE SPECIFIC EMBODIMENTS

Figure 1:
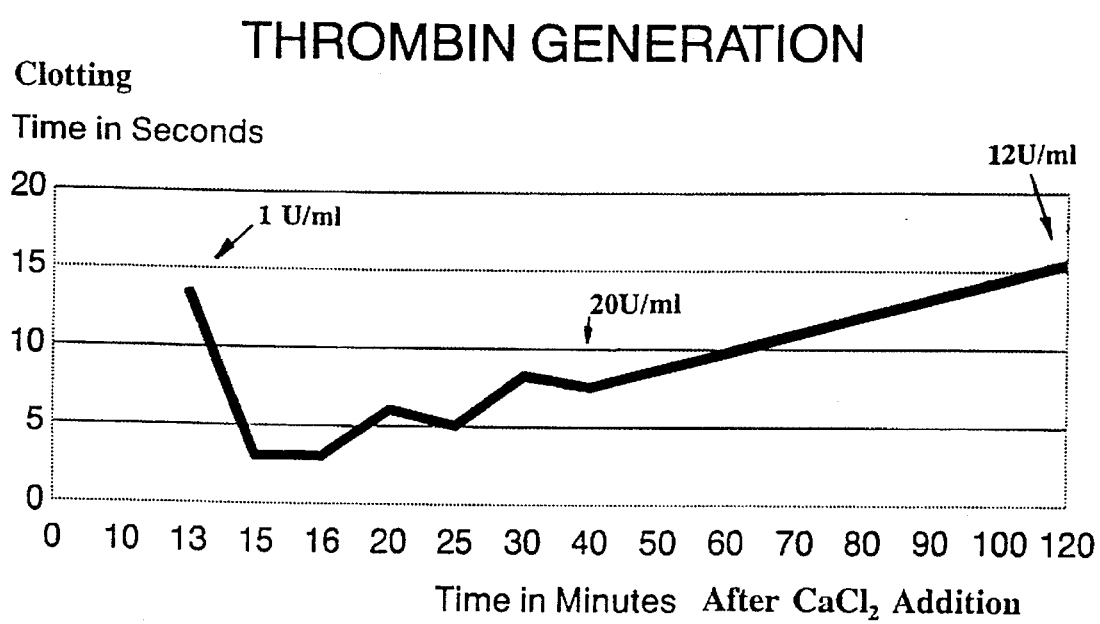
FIG. 1 is a plot showing thrombin activity (measured in clotting time) in thrombin compositions prepared by the method of the present invention over time.

Methods and compositions are provided for preparing fibrin glues from plasma obtained from a single donor. Often, but not always, the donor will also be the patient who receives the fibrin glue for hemostasis, tissue sealing, or the like. Procedures which rely on the patient as the donor will usually be surgical or other elective procedures that are scheduled in advance. In cases where the donor is the patient, there is of course no risk of the transmission of blood-born diseases. The use of fibrin glue obtained from a single donor is also advantageous when the donor is not the patient. It is much easier to screen a single donor for disease than to screen multiple donors who may contribute to pooled serum sources used to obtain fibrinogen for many previous fibrin glues.

Plasma will be obtained from the donor in a conventional manner. Blood, typically from 100 ml to 150 ml, will be obtained by phlebotomy, and cellular components will be removed by conventional techniques, such as centrifugation, to produce plasma, typically from 50 ml to 75 ml.

Fibrinogen is separated from the plasma by precipitation to produce a fibrinogen-containing precipitate and a thrombin-containing supernatant. Precipitation may be achieved in any conventional manner. Cryoprecipitation is preferred and may be carried out as follows. The plasma, typically having a volume of 40 ml to 50 ml is frozen at temperature in the range from $-70°$ C. to $-80°$ C. for a time in the range from 1 hour to 24 hours. After freezing, the plasma is thawed at $4°$ C. and subsequently centrifuged at from 4000 g to 5000 g for a short time, typically about 5 min to 10 min. The supernatant is then decanted, leaving the precipitate which contains most of the fibrinogen. Optionally, the fibrinogen precipitate may be resuspended in a small amount of the supernatant, typically about 3 ml to 5 ml. The fibrinogen suspension will then typically be collected in a syringe or other applicator for subsequent application to the patient. Typically, fibrinogen will have a concentration of at least 20 g/l, which represents an approximately ten-fold increase in concentration when compared to the original plasma. Methods for precipitating fibrinogen from plasma using polyethylene glycol or ammonium sulfate are well described in the literature. See, for example, Brennan (1991), supra.

After the fibrinogen has been precipitated the plasma supernatant is separated. The residual fibrinogen in the supernatant is removed by clotting (by the addition of $CaCl_2$ as described below) to produce serum containing thrombin and fibrin. The fibrin is then removed (e.g. by filtration) from the serum, and the resulting thrombin-containing serum is suitable for use as the thrombin component of the fibrin glue. Clotting of the residual fibrinogen is preferably accomplished by adding 0.1 volume of 0.2M calcium chloride. Removal of the fibrin is achieved by conventional filtration, or other separation techniques, such as centrifugation.

The thrombin component thus prepared has been found to have significant thrombin activity, both immediately following the clotting step and for one or more hours following the clotting step. Usually, the activity immediately following the clotting step will be at least about 5 U/ml, preferably being at least about 20 U/ml. After one hour, the remaining activity will usually be at least 2 U/ml, preferably being at least 5 U/ml.

The fibrinogen component and thrombin component of the fibrin glues of the present invention may be applied to a treatment site in a patient in a conventional manner. Typically, equal volumes of the fibrinogen component and the thrombin-component will be maintained separately until it is time to treat the patient. At that time, the components will be mixed and simultaneously applied to the treatment site. Specialized dual-cylinder syringes have been developed for such application. See, e.g., McCarthy (1993), supra and Brennan (1991), supra. The fibrinogen component and thrombin component may also be applied as a spray.

The following example is offered by way of illustration, not by way of limitation.

EXAMPLE

Ninety ml of autologous blood is taken into a pediatric bag containing 10 ml of citrate phosphate dextrose adenine solution. The blood is centrifuged at 2000 G at $4°$ C. for 15 minutes. The plasma is dispensed into a second bag with the aid of a press. The plasma bag is laid flat and frozen at $-70°$ C. After a period of time the bag is thawed at $4°$ C., and after the cryoprecipitate is formed, the bag is centrifuged at $0°$ C. for 10 min at 5000 G. The supernatant plasma is drained into a second bag and used to prepare thrombin-containing serum, as described below. Five ml of the supernatant plasma is retained in the cryoprecipitate bag to dissolve the fibrinogen at $37°$ C. The resultant fibrinogen is concentrated by a factor of 10. The supernatant plasma is clotted by adding 0.1 volume of calcium chloride. Clotting occurs in approximately 3 minutes to yield serum containing both thrombin and fibrin. The fibrin is trapped by a filter through which the serum is dispensed. The thrombin generated in the serum reaches a maximum concentration within 5 minutes and remains at sufficiently high concentrations to produce fast fibrin (used for serious bleeding) for 20 minutes. Thereafter, the thrombin concentration decays slowly but is still effective for 60 to 90 minutes to produce "slow fibrin" which is used for oozing vessels. An exemplary plot showing clotting time vs. time after $CaCl_2$ addition is shown in FIG. 1. The thrombin-containing serum and the fibrinogen-containing cryoprecipitate are kept separate until just before the fibrin glue is required. At that time, the serum and the cryoprecipitate are mixed, and the resulting fibrin applied to the bleeding site or wound site. A suitable applicator is a double syringe connected to a single nozzle designed to produce a fine spray when the two components are forced through it. The resulting fibrin forms a film when it makes contact with the wound.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

Although the foregoing invention has been described in some detail by way of illustration and example, for purposes of clarity of understanding, it will be obvious that certain changes and modifications may be practiced within the scope of the appended claims.

What is claimed is:

1. An improved fibrin glue of the type including a fibrinogen component recovered from a single donor in combination with a thrombin component, wherein the improvement comprises thrombin in the thrombin component obtained solely from the same single donor.

2. An improved fibrin glue as in claim 1, wherein the thrombin component is obtained by precipitating fibrinogen from donor plasma to produce a supernatant, and clotting residual fibrinogen to produce the thrombin component.

3. An improved fibrin glue as in claim 2, wherein the thrombin component has a thrombin activity greater than 20 U/ml immediately after clotting.

4. An improved fibrin glue as in claim 3, wherein the thrombin component has a thrombin activity greater than 10 U/ml one hour after clotting.

5. A method for preparing fibrin glue, said method comprising:

obtaining plasma from a single donor;

precipitating fibrinogen from the plasma to produce a precipitate containing fibrinogen and a supernatant containing thrombin;

separating the supernatant from the precipitate;

clotting residual fibrinogen in the supernatant obtained from the plasma of the same single donor to produce serum containing thrombin and fibrin; and separating the fibrin from the serum to produce thrombin-containing serum;

wherein the fibrinogen precipitate and thrombin-containing serum may be recombined to form the fibrin glue.

6. A method as in claim 5, wherein the fibrinogen is precipitated by cryoprecipitation, polyethylene glycol precipitation, or ammonium sulfate precipitation.

7. A method as in claim 5, wherein the fibrinogen concentration in the precipitate is at least 20 g/l.

8. A method as in claim 5, further comprising resuspending fibrinogen in the precipitate with a portion of the supernatant prior to combining with the thrombin-containing serum.

9. A method as in claim 5, wherein the fibrinogen is clotted in the supernatant by the addition of calcium chloride.

10. A method as in claim 5, wherein the thrombin-containing serum has a thrombin activity of at least about 5 U/ml immediately after clotting.

11. A method as in claim 10, wherein the thrombin-containing serum has a thrombin activity greater than 2 U/ml one hour after clotting.

12. A method for preparing a thrombin composition, said method comprising:

obtaining plasma from a single donor;

precipitating the plasma to produce a precipitate containing fibrinogen and a supernatant containing thrombin and residual fibrinogen;

clotting residual fibrinogen in the supernatant to produce serum containing thrombin and fibrin; and separating the fibrin from the serum obtained from the plasma of the same single donor to produce the thrombin composition.

13. A method as in claim 12, wherein the fibrinogen is clotted in the supernatant by the addition of calcium chloride.

14. A method as in claim 12, wherein the thrombin-containing serum has a thrombin activity greater than 5 U/ml immediately after clotting.

15. A method as in claim 14, wherein the thrombin-containing serum has a thrombin activity greater than 2 U/ml one hour after clotting.

* * * * *